United States Patent
Chin et al.

[11] 4,357,346
[45] Nov. 2, 1982

[54] N-HALOALKYL THIOBENZANILIDES AND THEIR USE AS FUNGICIDES

[75] Inventors: Hsiao-Ling M. Chin; Ferenc M. Pallos, both of Walnut Creek, Calif.

[73] Assignee: Stauffer Chemical Company, Westport, Conn.

[21] Appl. No.: 223,469

[22] Filed: Jan. 8, 1981

[51] Int. Cl.³ .................. C07C 83/10; A01N 31/08
[52] U.S. Cl. ........................ 424/298; 260/453 RW
[58] Field of Search .............. 260/453 RW; 424/298

[56] References Cited

FOREIGN PATENT DOCUMENTS 2557950  12/1975  Fed. Rep. of Germany ...... 260/453 RW

OTHER PUBLICATIONS

Rahoff & Rose, Organic Chemistry, Macmillan Company, New York, 1966, p. 234.

*Primary Examiner*—John M. Ford
*Assistant Examiner*—Robert C. Whittenbaugh
*Attorney, Agent, or Firm*—Michael J. Bradley

[57] ABSTRACT

N-haloalkyl thiobenzanilide compounds having the formula

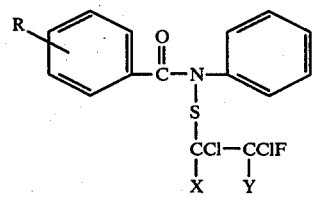

in which R is hydrogen, $C_1$–$C_5$ alkyl, preferably $C_1$–$C_3$ alkyl, $C_1$–$C_3$ haloalkyl, preferably —$CF_3$, halogen including —F, —Cl, —Br, and —I, —$NO_2$, $C_1$–$C_2$ alkoxy and X and Y are either —Cl or —F but not identical and their use as fungicides.

3 Claims, No Drawings

N-HALOALKYL THIOBENZANILIDES AND THEIR USE AS FUNGICIDES

This invention relates to certain novel N-haloalkyl thiobenzanilides which are useful as fungicides.

The compounds of the present invention correspond to the formula

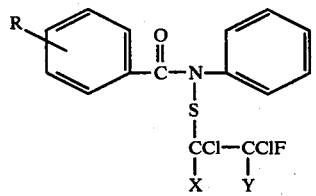

in which R is hydrogen, $C_1$–$C_5$ alkyl, preferably $C_1$–$C_3$ alkyl, $C_1$–$C_3$ haloalkyl, preferably —$CF_3$, halogen including —F, —Cl, —Br, and —I, —$NO_2$, $C_1$ to $C_2$ alkoxy and X and Y are either —Cl or —F but not identical.

Although the compounds of the invention are generally active as fungicides, it has been discovered that they are also effective as systemic toxicants and this ancillary feature greatly increases their usefulness and versatility in treating fungus-infected food crops. As those skilled in the art are aware, a systemic biocide is taken up internally by the organism to which it is applied and lodges in the tissues while still retaining toxicological properties. When used to protect food crops systemic toxicants are not subject to weathering since they are confined within the interstices of the plant tissues which are thereby internally immunized against the attack of harmful fungi, blights and similar pesticidal microorganisms.

The compounds of the present invention are prepared by the following general reaction.

Reaction No. 1

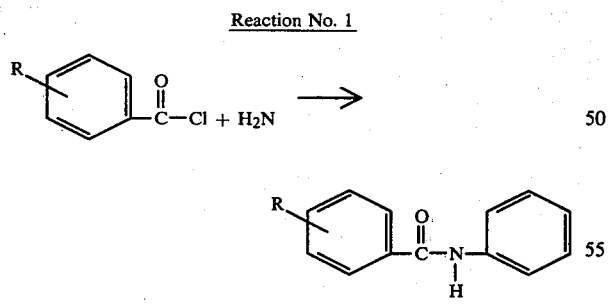

Generally a molar amount of the substituted benzoyl chloride reactant, dissolved in benzene, is added to a mixture of the aniline reactant and a slight molar excess of an HCl acceptor such as triethylamine. The mixture is refluxed for ½ hour and then cooled. The solid reaction product is diluted with a solvent such as ethyl acetate or chloroform and washed with water twice and salt solution once. The final product is dried over $MgSO_4$, filtered and evaporated.

Reaction No. 2

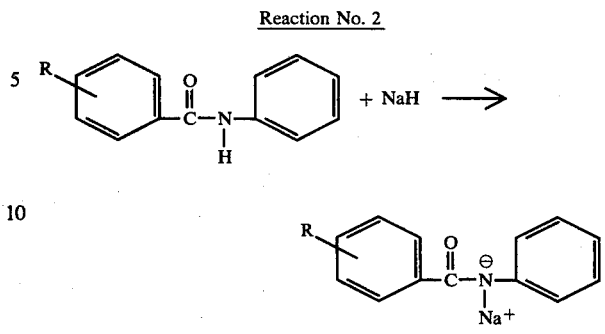

Under a dry nitrogen atmosphere a molar amount of the reaction product from Reaction No. 1 is dissolved in dry tetrahydrofuran (THF). Next, a slight molar excess of NaH is added with stirring. The mixture is refluxed for 1 hour and cooled.

Reaction No. 3

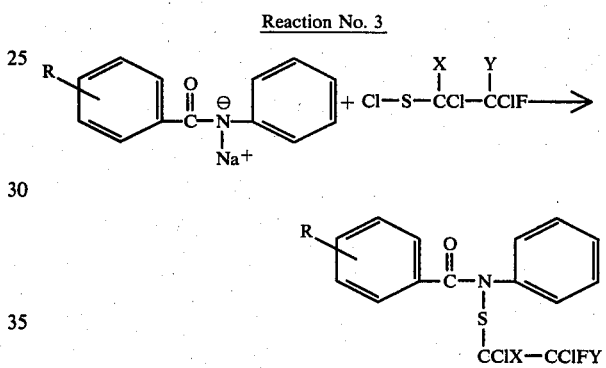

A molar amount of

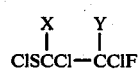

in THF is added dropwise to the reaction mixture of Reaction No. 2. The mixture is refluxed for 2½ hours and a large amount of $CH_2Cl_2$ is added to the solid reaction product. The product is washed twice with water, dried over $MgSO_4$ and evaporated.

The ClSCCl—CClF is prepared as outlined below:

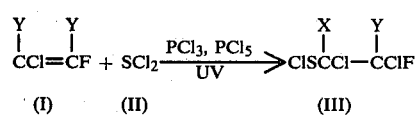

(I)   (II)   (III)

An equimolar mixture of Reagent I and Reagent II is irradiated under a U V lamp (at 8° C. to 60° C.) for 3 to 5 hours. The product III is isolated and purified by distillation under reduced pressure (40 mm Hg to 50 mm Hg).

Preparation of compounds of this invention is illustrated by the following examples.

EXAMPLE I

Preparation of 2-iodobenzoyl anilide

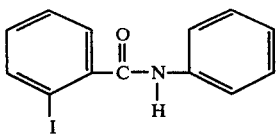

43.2 g. (0.464 moles) aniline and 46.9 g. triethylamine are mixed in 930 ml. benzene by stirring. A solution of 123.7 g. (0.464 moles) 2-iodobenzoyl chloride in 450 ml. benzene is added to the first mixture through a dropping funnel. An exothermic reaction takes place. After the addition is finished, the mixture is refluxed for ½ hour. The mixture is cooled and the product solidifies. The product is filtered, added to water, and stirred to dissolve triethylamine hydrochloride. The product is filtered again and dried to yield 146.8 g. of the desired product. (98% yield) m.p. 141°–144° C.

EXAMPLE II

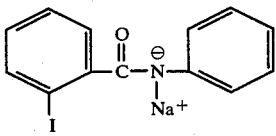

8.075 g. (0.025 moles) of the amide reaction product of Example I is dissolved in 60 ml. of dry THF under a dry nitrogen atmosphere. 0.66 g. (0.0275 moles) NaH is added to the mixture with stirring. The mixture is refluxed for one hour and then cooled.

EXAMPLE III

N-1,1,2-trichloro-2,2-difluoromethylthio-o-iodobenzanilide

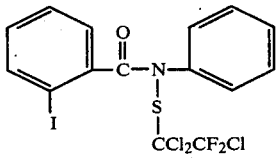

(0.025 moles) of ClSCCl$_2$CF$_2$Cl dissolved in 12 ml. THF is added dropwise to the cooled reaction mixture of Example II. The mixture is then refluxed for 2½ hours. Next 150 ml. CH$_2$Cl$_2$ is added, the mixture is washed twice with water, dried over MgSO$_4$ and evaporated to yield the desired product.

The following is a table of certain selected compounds that are preparable according to the procedure described herein. Compound numbers are assigned to each compound and are used throughout the remainder of the application.

TABLE I

| Compound Number | R | X | Y | Physical Constants m.p. or $n_D^{30}$ |
|---|---|---|---|---|
| 1 | 2-I | Cl | F | glassy solid |
| 2 | H | Cl | F | semi-solid |
| 3 | H | F | Cl | 1.5772 |
| 4 | 2-CF$_3$ | F | Cl | 1.5345 |
| 5 | 2-CF$_3$ | Cl | F | 1.5410 |
| 6 | 2-I | F | Cl | 1.6034 |
| 7 | 2-OCH$_3$ | F | Cl | 1.5698 |

Foliar Fungicide Evaluation Tests

A. Evaluation for Preventive Action

1. Bean Rust Test:

Pinto bean plants (*Phaseolus vulgaris* L.) approximately 10 centimeters (cm.) tall are transplanted into sandy loam soil in three-inch clay pots. The plants are then inverted and dipped for two to three seconds in 50—50 acetone/water solution of the test chemical. Test concentrations range from 1000 ppm downward. After the leaves are dried, they are inoculated with a water suspension of spores of the bean rust fungus (*Urumyces phaseoli* Arthur) and the plants are placed in an environment of 100% humidity for 24 hours. The plants are then removed from the humidity chamber and held until disease pustules appear on the leaves. Effectiveness is recorded as the lowest concentration, in ppm, which will provide 75% or greater reduction in pustule formation as compared to untreated, inoculated plants. These values are recorded in Table II.

2. Bean Powdery Mildew Test:

A candidate chemical is prepared and applied in the same manner as for the bean rust test. After the plants are dry, the leaves are dusted with spores of the powder mildew fungus (*Erysiphe polygoni* De Candolle) and the plants are retained in the greenhouse until the fungal growth appears on the leaf surface. Effectiveness is recorded as the lowest concentration, in ppm, which will provide 75% or greater reduction in mycelial formation as compared to untreated, inoculated plants. These values are recorded in Table II.

3. Tomato Early Blight:

A candidate compound is dissolved in an appropriate solvent and diluted with a 50—50 acetone water solution. Four week old tomato (*Lycopersicon esculentum*) plants are then sprayed with the solution to the point of runoff. Test concentrations range from 1000 ppm downward. When the leaves are dry, they are inoculated with a water suspension of spores of the early blight fungus (*Alternaria solani* Ellis and Martin) and placed in an environment of 100% humidity for 48 hours. The plants are then removed from the humidity chamber and held until disease lesions appear on the leaves. Effectiveness is recorded as the lowest concentration, in ppm, which will provide 75% or greater reduction in the number of lesions formed as compared to untreated, inoculated plants. These values are recorded in Table II.

4. Blue Grass Leaf Spot:

A candidate chemical is prepared and applied in the same manner as the tomato early blight test except that four week old Kentucky Bluegrass (*Poa pratensis*) plants are utilized as the host plant. When the leaves are dry, they are inoculated with a water suspension of spores of the blue grass leaf spot fungus (*Helminthosporium sativum*) and placed in an environment of 100% humidity for 48 hours. The plants are then removed from the humidity chamber and held until disease lesions appear on the leaves. Effectiveness is recorded as the lowest concentration, in ppm, which will provide 75% or greater reduction in number of lesions formed as compared to untreated, inoculated plants. These values are recorded in Table II.

B. Evaluation for Eradicant Action

1. Bean Rust Test:

Untreated bean plants (*Phaseolus vulgaris* L.) are inoculated with spores of the bean rust fungus (*Uromyces phaseoli* Arthur) and placed in an environment with 100% humidity for 24 hours. The plants are then removed from the humidity chamber and held in the greenhouse for two days to allow the disease to become established. A candidate chemical is then prepared and applied in the same manner as in the bean rust test in "Evaluation for Preventive Action". Eradicative effectiveness is recorded as the lowest concentration, in ppm, which will provide a 75% or greater reduction in number of pustules appearing on the leaves as compared to untreated inoculated plants. These values are recorded in Table II.

2. Bean Powdery Mildew Test:

Untreated pinto bean plants are dusted with spores of the powdery mildew fungus (*Erysiphe polygoni* De Candolle) and maintained in the greenhouse until mycelial growth appears in the leaf surface. A candidate chemical is then prepared and applied in the same manner as for the bean rust test. Four days later the leaves are examined for inhibition of further mycelial growth. Eradicative effectiveness is recorded as the lowest concentration, in ppm, which will provide a 75% or greater inhibition of viable, sporulating mycelium as compared to untreated inoculated plants. These values are recorded in Table II.

TABLE II

| | Preventive Action | | | |
|---|---|---|---|---|
| Compound Number | Bean Rust | Bean Powdery Mildew | Tomato Early Blight | Blue Grass Leaf Spot |
| 1 | 10 | 100 | 100 | 25 |
| 2 | 25 | 50 | 50 | 25 |
| 3 | 50 | 50 | 25 | 25 |
| 4 | 25 | 100 | 50 | 50 |
| 5 | 10 | 100 | 50 | 100 |
| 6 | 10 | 100 | 50 | * |
| 7 | 50 | 50 | 50 | 100 |

*No control at 1000 ppm and not tested at higher concentrations.

| | Eradicant Action | | | |
|---|---|---|---|---|
| 1 | 1 | >50 | | |
| 2 | >50 | >50 | | |
| 3 | >50 | >50 | | |
| 4 | 0.5 | 50 | | |
| 5 | 0.5 | (50) | | |
| 6 | 0.5 | >50 | | |
| 7 | — | — | | |

( ) Indicates partial control.

The compounds of this invention are generally embodied into a form suitable for convenient application. For example, the compound can be embodied into a pesticidal composition which is provided in the form of emulsions, suspensions, solutions, dusts and aerosol sprays. In general, such compositions will contain, in addition to the active compound, the adjuvants which are found normally in pesticide preparations. In these compositions, the active compound of this invention can be employed as the sole pesticide component or it can be used in admixture with other compounds having similar utility. The pesticide compositions of this invention can contain, as adjuvants, organic solvents, such as sesame oil, xylene range solvents, heavy petroleum, etc.; water; emulsifying agents; surface active agents; talc; pyrophyllite; diatomite; gypsum; clays, propellants, such as dichlorodifluoromethane, etc. If desired, however, the active compound can be applied directly to feedstuffs, seeds, etc., upon which the pests feed. When applied in such a manner, it will be advantageous to use a compound which is not volatile. In connection with the activity of the presently disclosed pesticidal compound, it should be fully understood that it is not necessary that they be active as such. The purposes of this invention will be fully served if the compound is rendered active by external influences, such as light or by some physiological action which occurs when the compound is ingested into the body of the pest.

The precise manner in which the pesticidal compositions of this invention are used in any particular instance will be readily apparent to a person skilled in the art. Generally, the active pesticide compound will be embodied in the form of a liquid composition; for example, an emulsion, suspension, or aerosol spray. While the concentration of the active pesticide in the present compositions can vary within rather wide limits, ordinarily the pesticide compound will comprise not more than about 15.0% by weight of the composition. Preferably, however, the pesticide compositions of this invention will be in the form of solutions or suspensions containing about 0.1 to 1.0% by weight of the active pesticide compound.

What is claimed is:

1. A compound having the formula

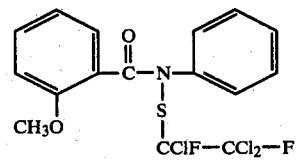

2. A method of controlling fungi comprising applying thereto a fungicidally effective amount of a compound having the formula

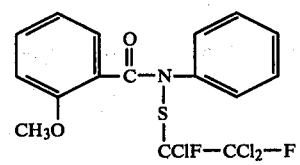

3. A fungicidal composition of matter comprising a fungicidally effective amount of a compound having the formula

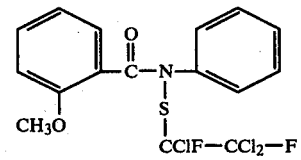

and an inert diluent carrier.

* * * * *